US009018157B2

(12) United States Patent
Wang

(10) Patent No.: US 9,018,157 B2
(45) Date of Patent: Apr. 28, 2015

(54) PREVENTION AND TREATMENT OF INFLAMMATION AND ORGAN INJURY AFTER ISCHEMIA/REPERFUSION USING MFG-E8

(75) Inventor: Ping Wang, Roslyn, NY (US)

(73) Assignee: The Feinstein Institute for Medical Research, Manhassett, NY (US)

( * ) Notice: Subject to any disclaimer, the term of this patent is extended or adjusted under 35 U.S.C. 154(b) by 48 days.

(21) Appl. No.: 12/734,596

(22) PCT Filed: Nov. 13, 2008

(86) PCT No.: PCT/US2008/012761
§ 371 (c)(1),
(2), (4) Date: May 11, 2010

(87) PCT Pub. No.: WO2009/064448
PCT Pub. Date: May 22, 2009

(65) Prior Publication Data
US 2011/0105399 A1    May 5, 2011

Related U.S. Application Data

(60) Provisional application No. 61/003,478, filed on Nov. 15, 2007.

(51) Int. Cl.
A61K 38/37    (2006.01)
A61K 38/18    (2006.01)
C07K 14/485   (2006.01)

(52) U.S. Cl.
CPC ............. *A61K 38/37* (2013.01); *A61K 38/1808* (2013.01); *C07K 14/485* (2013.01)

(58) Field of Classification Search
None
See application file for complete search history.

(56) References Cited

U.S. PATENT DOCUMENTS

2004/0241179 A1* 12/2004 Raposo et al. ............. 424/185.1
2009/0297498 A1  12/2009 Wang
2014/0121163 A1   5/2014 Wang

FOREIGN PATENT DOCUMENTS

| WO | WO 95/15171 A1 | 6/1995 |
| WO | WO 03/043649 A1 | 5/2005 |
| WO | WO 2005/077397 A2 | 8/2005 |
| WO | 2006122327 A2 | 11/2006 |
| WO | 2006124770 A2 | 11/2006 |
| WO | WO 2006/122327 A2 | 11/2006 |
| WO | WO 2006/124770 A2 | 11/2006 |

OTHER PUBLICATIONS

Miksa et al. Shock 2006 25:586-593.*
Rudinger Characteristics of the amino acids as components of a peptide hormone sequence. "Peptide Hormones", JA Parsons, Ed., Baltimore:University Park Press 1976, 1-7.*
Sigma Genosys reference www.sigma-biosys.com/peptide_design.asp 2004.*
Schinzel et al. FEBS 1991 286: 125-128.*
Voet et al. Biochemistry New York:John Wiley and Sons, Inc., 1995 235-241.*
Lopes et al. Evolutionary algorithms for the protein folding problem: a review and current trends. "Computational Intelligence in Biomedicine and Bioinformatics" Smolinski et al., Ed., Berlin:Springer-Verlag 2008, 297-315.*
Berendsen Science 1998 282:642-643.*
Dill et al. Current Opinion in Structural Biology 2007 17:342-346.*
Murphy et al. Experimental models and endpoints for studies of intestinal ischemia-reperfusion injury "Surgical Research" Souba et al. Ed. San Diego:Academic Press 2001 583-585.*
Popovsky et al. Transfusion 1985 25:573-577.*
Koksoy et al. British Journal of Surgery 2001 88:464-468.*
R&D Systems Cytokine Bulletin Spring 1996.*
Lane et al. Surgery 1997 122:288-294.*
Stubbs et al. Proceedings of the national Academy of Sciences USA 1990 87:8417-8421.*
Linfert et al. Transplant Reviews 2009 23(1):1-10.*
Collard et al. Anesthesiology 2001 94(6):1133-1138.*
Pierro et al. Seminars in Pediatric Surgery 2004 13(1):11-17.*
Weight et al. British Journal of Surgery 1996 83:162-170.*
White et al. Journal of Neurological Sciences 2000 179:1-33.*
Lee et al. Critical Care Medicine 2012 40(11):2997-3006.*
Hanayama et al. Nature 2002 417:182-187.*
Seekamp et al. American Journal of Pathology 1993 143(2)453-463.*
Colletti et al. Journal of Clinical Investigation 1990 85:1936-1943.*
Arvin et al. Neuroscience and Biobehavioral Reviews 1996 20(3):445-452.*
The Supplementary European Search Report dated Jan. 19, 2011 for European Application No. EP 08 84 8811.9.
Zhong et al. "Neovascularization of Ischemic Tissues by Gene Delivery of the Extracellular Matrix Protein Del-1." The J. of Clin. Invest. (Jul. 2003) 112:1, pp. 30-41.
Ho et al. "Developmental Endothelial Locus-1 (Del-1), a Novel Angiogenic Protein: Its Role in Ischemia." Circulation (Mar. 2004), pp. 1314-1318.
Silvestre et al. "Lactadherin Promotes VEGF-dependent Neovascularization." Nature Medicine, vol. 11, No. 5 (May 2005), pp. 499-506.

(Continued)

Primary Examiner — Juliet Switzer
Assistant Examiner — Caralynne Helm
(74) Attorney, Agent, or Firm — Amster, Rothstein & Ebsenstein LLP

(57) ABSTRACT

Provided are methods for preventing and treating inflammation and organ injury after ischemia/reperfusion, and methods for treating lung injury, comprising administering a milk fat globule epidermal growth factor-factor VIII (MFG-E8) to a subject. Also provided are pharmaceutical compositions comprising MFG-E8 in dosage form for preventing and treating inflammation and organ injury after ischemia/reperfusion, and for treating lung injury, and methods of preparing a pharmaceutical composition for preventing and treating inflammation and organ injury after ischemia/reperfusion, and for treating lung injury, comprising formulating MFG-E8 in a pharmaceutical composition.

16 Claims, 8 Drawing Sheets

(56) References Cited

OTHER PUBLICATIONS

Hanayama R et al., entitled "Impaired involution of mammary glands in the absence of milk fat globule EGF factor 8," PNAS, vol. 102, No. 46, Nov. 15, 2005, 16886-16891.

PCT Notification of Transmittal of the International Search Report and The Written Opinion of The International Searching Authority, or the Declaration dated Feb. 17, 2009 by the U.S. Patent Office in connection with PCT International Patent Application No. PCT/US2008/012761, 10 pages.

EPO Communication pursuant to Article 94(3) EPC, dated Dec. 6, 2011, issued in connection with European Application No. 08848811.9.

Chinese Office Action dated Apr. 1, 2012, issued in Chinese Patent Application No. 200880122777.8 with English Translation, Translated portions were considered.

Communication pursuant to Article 94(3) EPC dated May 24, 2014 from the European Patent Office in connection with European Patent Application No. 08 848 811.9, 3 pages.

Translation of Chinese Office Action dated Nov. 18, 2013 from the Chinese Patent Office in connection with Chinese Patent Application No. 200880122777.8, 11 pages.

* cited by examiner

PREVENTION AND TREATMENT OF INFLAMMATION AND ORGAN INJURY AFTER ISCHEMIA/REPERFUSION USING MFG-E8

CROSS-REFERENCE TO RELATED APPLICATIONS

This application is a national stage entry under 35 U.S.C. §371 of PCT International Patent Application No. PCT/US2008/012761, filed Nov. 13, 2008, and claims priority to U.S. Provisional Patent Application No. 61/003,478, filed Nov. 15, 2007, the contents of which are incorporated herein by reference in their entirety into the subject application.

STATEMENT OF GOVERNMENT SUPPORT

The invention was made with government support under grant GM057468 awarded by the National Institutes of Health. The government has certain rights in this invention.

FIELD OF THE INVENTION

The present invention relates to using milk fat globule EGF-factor 8 (MFG-E8) for prevention and treatment of inflammation and organ injury after ischemia/reperfusion, especially after gut or intestinal ischemia/reperfusion, and for treatment of lung injury, such as acute lung injury.

BACKGROUND OF THE INVENTION

Throughout this application various publications are referred to in parenthesis. Full citations for these references may be found at the end of the specification preceding the claims. The disclosures of these publications are hereby incorporated by reference in their entireties into the subject application to more fully describe the art to which the subject application pertains.

Reperfusion injury refers to damage to tissue caused when blood supply returns to the tissue after a period of ischemia. Intestinal ischemia can occur in a variety of clinical conditions, including small bowel transplant, superior mesenteric artery occlusion, cardiac insufficiency with associated low flow state, and hemorrhagic shock and necrotizing enterocolitis.

Mesenteric ischemia remains a critical problem, resulting in a mortality as high as 60-80% (1). Multiple organ failure, including acute lung injury (ALI) is a common complication of intestinal ischemia/reperfusion (I/R) injuries and contributes to its high death toll (2). ALI is caused by a systemic inflammatory response due to the release of pro-inflammatory cytokines and bacteria-derived endotoxins from reperfused ischemic tissue (3-6). So far, only a limited number pharmacologic treatment options have been found that provide some benefit in I/R and acute lung injury, most of them targeting inflammatory mediators and oxidative stress pathways (7). A key aspect of I/R injury is the increased occurrence of apoptotic cell death of intestinal and bronchial epithelial cells and of type II alveolar macrophages (2, 8-11). Apoptosis is associated by a marked up-regulation of Fas and Fas-ligand, and the activation of caspase-3 in lung epithelial cells (12, 13). Proinflammatory cytokines like IL-1β or TNF-α seem to play a major role in apoptosis induction involving Bid, Bax upregulation and Bcl-2 downregulation (9, 14, 15).

While balanced apoptosis and phagocytosis maintain normal function, deficient clearance of apoptotic cells after ischemia potentially leads to increased inflammation and impaired tissue repair (16, 17). Apoptotic cells expose phosphatidylserine (PS) that can be recognized by soluble molecules and receptors, thereby enabling their phagocytosis (18). One of these molecules is milk fat globule EGF-factor 8 (MFG-E8), which is crucial for apoptotic cell clearance (19). Hanayama et al. found for example that the effective clearance of apoptotic B-cells in the spleen prevents inadequate pro-inflammatory immune responses and the development of auto-antibodies (20). In a rat sepsis model using cecal ligation and puncture, MFG-E8 is downregulated in spleens and livers. This was associated with impaired apoptotic cell clearance and increased mortality in these animals (21). Similar to sepsis, gut I/R injury is accompanied by a systemic inflammatory response.

Milk fat globule EGF-factor 8 (MFG-E8) is a potent opsonin for the clearance of apoptotic cells and is produced by mononuclear cells of immune competent organs including the spleen and lungs. Ischemia-reperfusion (I/R) injuries of the gut induce apoptosis, severe inflammation, and remote organ damage including acute lung injury (ALI). Whether enhancing apoptotic cell clearance is beneficial under such conditions has been unknown. There is a clear need for improved treatment and prevention of I/R injuries.

SUMMARY OF THE INVENTION

The invention is directed to methods of preventing and/or treating inflammation and/or organ injury after ischemia/reperfusion in a subject comprising administering to the subject milk fat globule epidermal growth factor-factor VIII (MFG-E8) in an amount effective to prevent and/or treat inflammation and/or organ injury.

The invention is also directed to pharmaceutical compositions comprising milk fat globule epidermal growth factor-factor VIII (MFG-E8) in dosage form for preventing and/or treating inflammation and/or organ injury after ischemia/reperfusion.

The invention further provides methods of preparing a pharmaceutical composition for preventing and/or treating inflammation and/or organ injury after ischemia/reperfusion, the method comprising formulating milk fat globule epidermal growth factor-factor VIII (MFG-E8) in a pharmaceutical composition in an amount effective to prevent and/or treat inflammation and/or organ injury after ischemia/reperfusion.

The invention also provides methods of treating lung injury, such as acute lung injury, in a subject comprising administering to the subject a milk fat globule epidermal growth factor-factor VIII (MFG-E8) in an amount effective to treat lung injury in the subject.

The invention provides pharmaceutical compositions comprising milk fat globule epidermal growth factor-factor VIII (MFG-E8) in dosage form for treating lung injury.

The invention further provides methods of preparing pharmaceutical compositions for treating lung injury, the methods comprising formulating milk fat globule epidermal growth factor-factor VIII (MFG-E8) in a pharmaceutical composition in an amount effective to treat lung injury.

MFG-E8 protein levels were assessed by Western blot. Data are expressed as means±SEM, *P<0.05 vs. Sham by Student's t-test, n=6.

FIG. 2A-2F. Attenuation of organ injury by recombinant murine MFG-E8 (rmMFG-E8) after intestinal I/R. The SMA was occluded for 90 min followed by 4 h of reperfusion. (A) H&E staining of the small intestine after intestinal I/R revealed widespread mucosal injury (middle panel), while treatment with rmMFG-E8 showed beneficial local effects (right panel). Left panel: sham control. (B) Lactate, (C) LDH, (D) ALT, (E) AST, and (F) creatinine were measured 4 h after reperfusion. Data are expressed as means±SEM, *P<0.05 vs. Sham, #P<0.05 vs. Vehicle by One-Way ANOVA and Student Newman Keul's test, n=6.

Figures 3A, 3B, 3C:
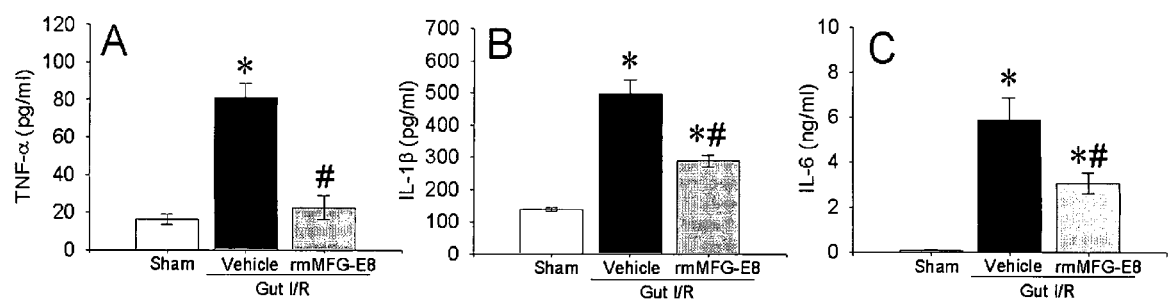

FIG. 3A-3C. Suppression of plasma cytokines by rmMFG-E8 after intestinal I/R. The SMA was occluded for 90 min followed by 4 h of reperfusion. Blood cytokines (TNF-α, IL-1β, and IL-6) were assessed by ELISA. Data are expressed as means±SEM, *P<0.05 vs. Sham, #P<0.05 vs. Vehicle by One-Way ANOVA and Student Newman Keul's test, n=6.

Figures 4A, 4B, 4C:
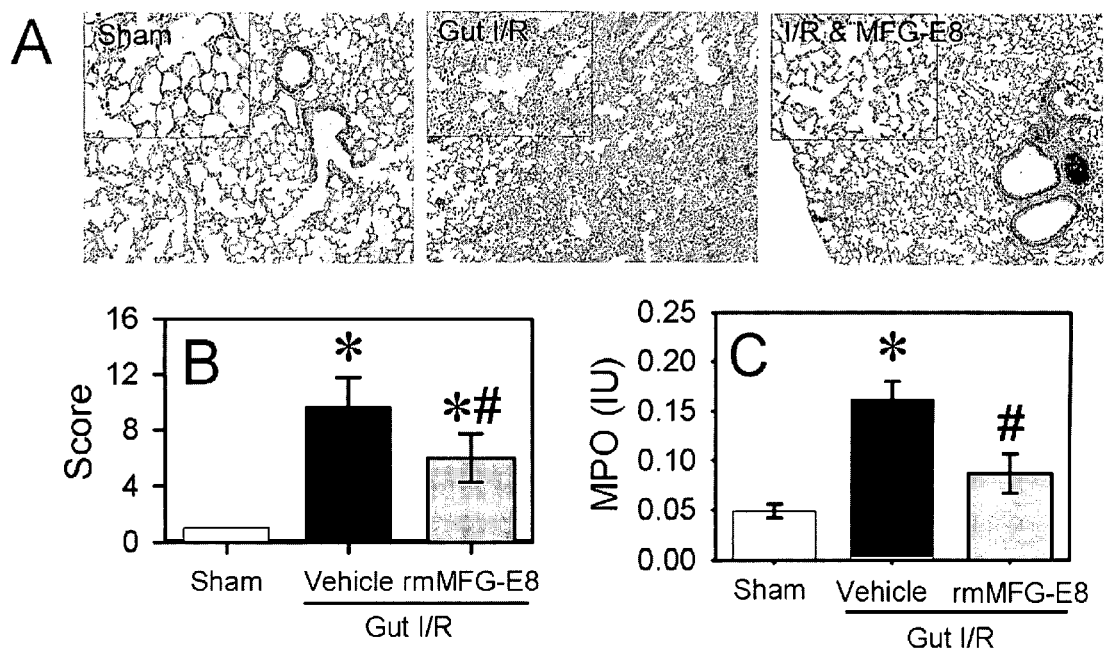

FIG. 4A-4C. Attenuation of acute lung injury (ALI) by rmMFG-E8. The SMA was occluded for 90 min followed by 4 h of reperfusion. Lungs were fixed and stained with H&E. (A) Representative micrographs at original 100× and 400× magnification (inlet). (B) Tissue injury was scored as described in the methods section. (C) Neutrophil activity was assessed by MPO assay. Data are expressed as means±SEM, *P<0.05 vs. Sham, #P<0.05 vs. Vehicle by One-Way ANOVA and Student Newman Keul's test, n=6.

Figures 5A, 5B, 5C:
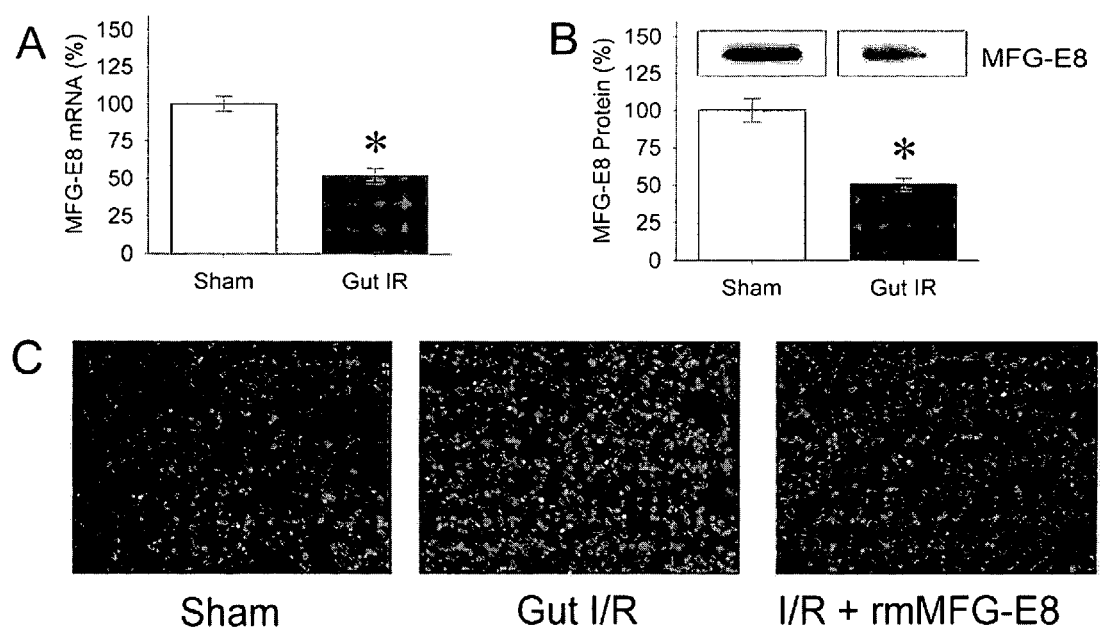

FIG. 5A-5C. Decreased pulmonary MFG-E8 after intestinal I/R and restoration of apoptotic cell clearance by rmMFG-E8 treatment. (A) MFG-E8 mRNA levels were measured by qPCR, (B) MFG-E8 protein levels were assessed by Western blotting. Data are expressed as measns±SEM, *P<0.05 vs. Sham by Student's t test, n=6. (C) Lungs were stained with TUNEL and counterstained with propidium iodine.

Figure 6A:
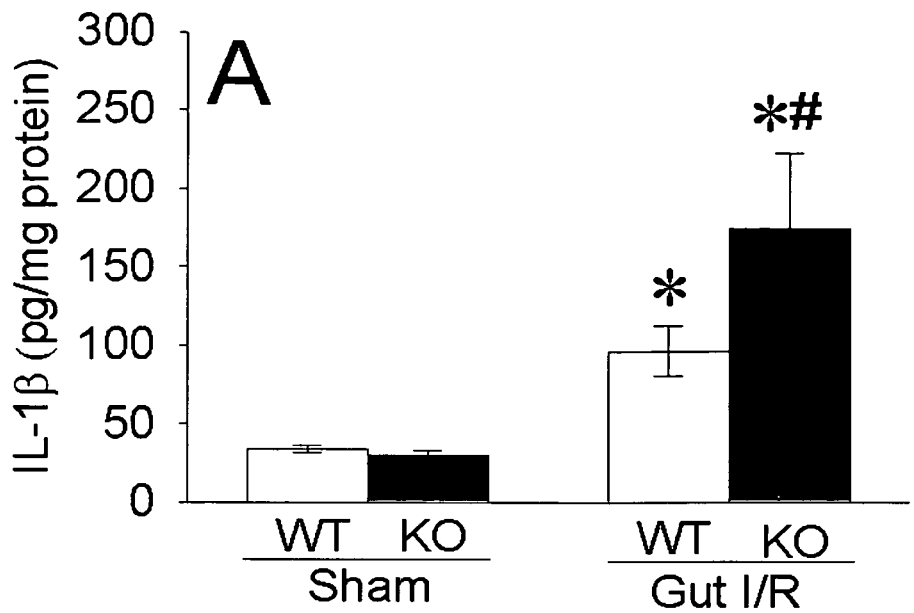
Figure 6B:
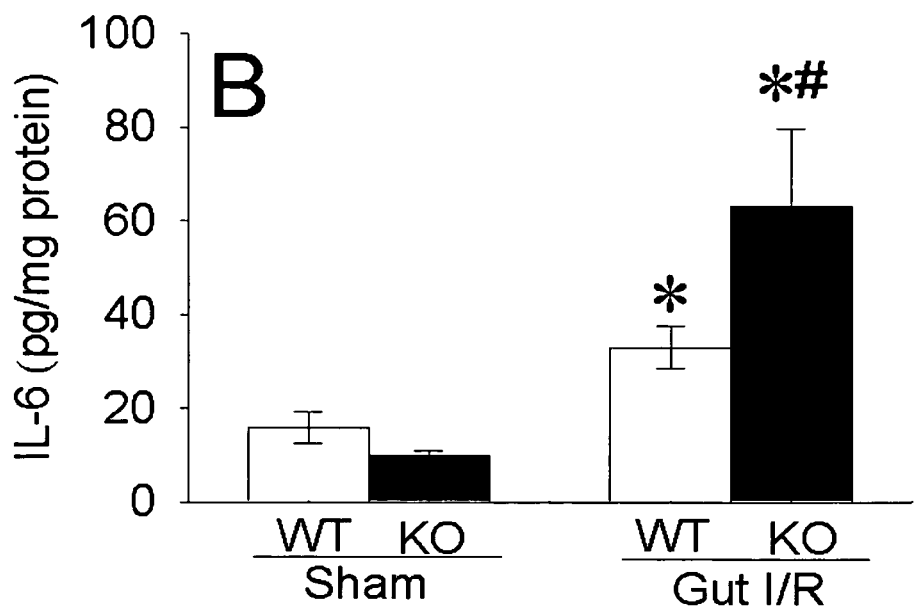

FIG. 6A-6B. MFG-E8 deficiency worsens the inflammatory response in the lung of mice after gut I/R. 4 h after reperfusion, pulmonary tissues were collected and assessed for (A) IL-1β and (B) IL-6. Data are expressed as measns±SEM, *P<0.05 vs. Sham, #P<0.05 vs. WT by Two-Way ANOVA and Student Newman Keul's test, n=6. WT: wild-type mice; KO: knockout mice.

Figures 7A, 7B, 7C:
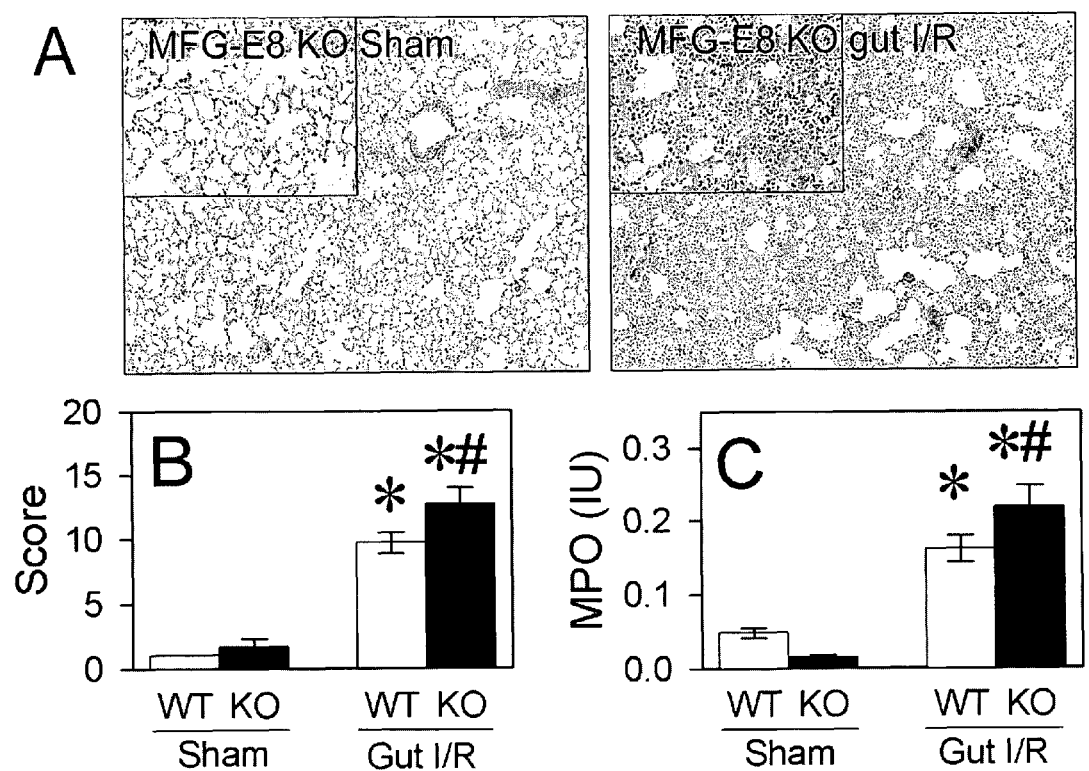

FIG. 7A-7C. MFG-E8 deficiency deteriorates ALI. 5 The SMA was occluded for 90 min followed by 4 h of reperfusion. Lungs were fixed and stained with H&E. (A) Microphotographs at original 100× and 400× magnification (inlet). (B) Tissues were scored as described in the methods section. (C) Neutrophil activity was assessed by MPO assay. Data are expressed as means±SEM, *P<0.05 vs. Sham, #P<0.05 vs. WT by Two-Way ANOVA and Student Newman Keul's test, n=6.

Figure 8:
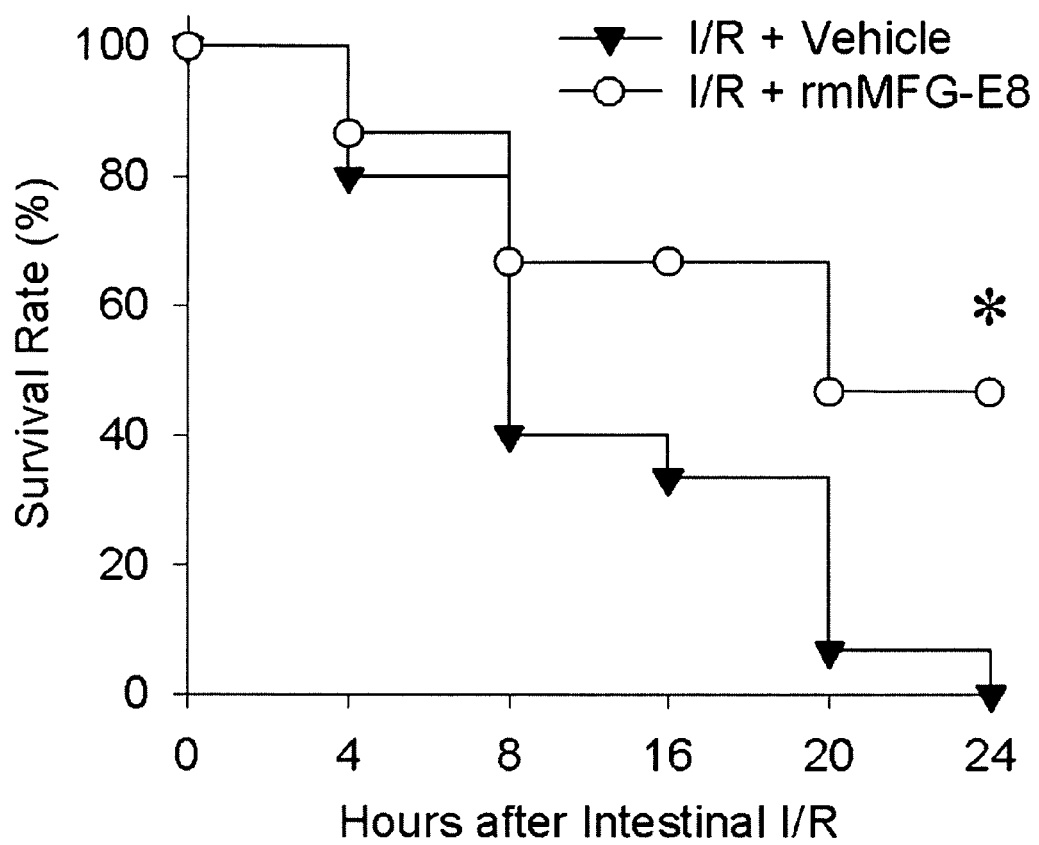

FIG. 8. Survival benefit in rmMFG-E8-treated mice after gut I/R injury. The SMA was occluded for 90 min followed by 4 h of reperfusion. Each group of mice received one dose of rmMFG-E8 or normal saline (vehicle) i.p. at the beginning of reperfusion and was observed for 24 h. *P<0.05 vs. Vehicle by Kaplan Meyer Log-rank test, n=15.

DETAILED DESCRIPTION OF THE INVENTION

The invention is directed to a method of preventing and/or treating inflammation and/or organ injury after ischemia/reperfusion in a subject comprising administering to the subject a milk fat globule epidermal growth factor-factor VIII (MFG-E8) in an amount effective to prevent and/or treat inflammation and/or organ injury. Ischemia/reperfusion includes, but is not limited to, ischemia/reperfusion of the gastrointestinal tract, liver, lung, kidney, heart, brain, spinal cord and/or crushed limb. In particular, the invention is directed to a method of preventing and/or treating inflammation and/or organ injury after intestinal ischemia/reperfusion in a subject comprising administering to the subject a milk fat globule epidermal growth factor-factor VIII (MFG-E8) in an amount effective to prevent and/or treat inflammation and/or organ injury.

Preferably, the method prevents or reduces serum elevation of one or more of tumor necrosis factor-α, interleukin-6, interleukin-1β, aspartate aminotransferase, alanine aminotransferase, lactate, or lactate dehydrogenase.

Preferably, the organs in which organ injury is prevented or treated include, but are not limited to, one or more of gastrointestinal tract, liver, lung, kidney, heart, brain, spinal cord, and crushed limb. The lung injury can be acute lung injury (ALI).

Preferably, the survival of the subject is improved.

Preferably, the MFG-E8 has an amino acid sequence at least 80%, more preferably at least 90%, even more preferably 95%, still more preferably, at least 99% identical to SEQ ID NO:1 or SEQ ID NO:2, which are the sequences of a human MFG-E8 and mouse MFG-E8, respectively. Most preferably, the MFG-E8 sequence is completely homologous to SEQ ID NO:1. These methods can be used with any mammal, including humans.

The MFG-E8 in these embodiments can be in purified form, e.g., as a protein purified from a natural source or as a transgenic protein expressed from a recombinant cell. Alternatively, the MFG-E8 can be only partially purified (e.g., further comprising cellular components, such as in the form of MFG-E8-rich exosomes derived from bone marrow dendritic cells or from other mammalian cells, including cells transformed with transgenic MFG-E8). Where the MFG-E8 is from MFG-E8-rich exosomes, the exosomes are preferably from the same species as the treated mammal; more preferably, the exosomes are from the same individual. The MFG-E8 can have a wild-type sequence from any mammalian species, or can comprise mutations, provided the mutations do not eliminate the protein's activity to prevent and/or treat inflammation and/or organ injury. Such mutants could be made without undue experimentation. The activity of those mutants can also be easily determined by known methods and the methods described herein.

The MFG-E8 can also comprise peptidomimetics. As used herein, an amino acid mimetic or peptidomimetic is a compound that is capable of mimicking a natural parent amino acid in a protein, in that the substitution of an amino acid with the peptidomimetic does not significantly affect the activities of interest of the protein, in this case, the therapeutic activity of exogenous MFG-E8. Proteins comprising peptidomimetics are generally poor substrates of proteases and are likely to be active in vivo for a longer period of time as compared to the natural proteins. In addition, they could be less antigenic and show an overall higher bioavailability. The skilled artisan would understand that design and synthesis of aqueous-soluble proteins comprising peptidomimetics would not require undue experimentation (e.g., 39-41).

The invention also provides a pharmaceutical composition comprising milk fat globule epidermal growth factor-factor VIII (MFG-E8) in dosage form for preventing and/or treating inflammation and/or organ injury after ischemia/reperfusion. Ischemia/reperfusion includes, but is not limited to, ischemia/reperfusion of the gastrointestinal tract, liver, lung, kidney, heart, brain, spinal cord and/or crushed limb. Intestinal ischemia/reperfusion is a preferred form of ischemia/reperfusion.

The invention further provides a method of preparing a pharmaceutical composition for preventing and/or treating inflammation and/or organ injury after ischemia/reperfusion, the method comprising formulating milk fat globule epidermal growth factor-factor VIII (MFG-E8) in a pharmaceutical composition in an amount effective to prevent and/or treat inflammation and/or organ injury after ischemia/reperfusion. Ischemia/reperfusion includes, but is not limited to, ischemia/reperfusion of the gastrointestinal tract, liver, lung, kidney, heart, brain, spinal cord and/or crushed limb. Intestinal ischemia/reperfusion is a preferred ischemia/reperfusion.

The above-described MFG-E8 preparations are preferably formulated in a pharmaceutical composition. These compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

The invention also provides for the use of milk fat globule epidermal growth factor-factor VIII (MFG-E8) for preventing and/or treating inflammation and/or organ injury after ischemia/reperfusion. The invention further provides for the use of milk fat globule epidermal growth factor-factor VIII (MFG-E8) for the preparation of a pharmaceutical composition for preventing and/or treating inflammation and/or organ injury after ischemia/reperfusion.

The invention also provides methods of treating lung injury, such as for example, acute lung injury, in a subject comprising administering to the subject a milk fat globule epidermal growth factor-factor VIII (MFG-E8) in an amount effective to treat lung injury in the subject. The invention provides pharmaceutical compositions comprising milk fat globule epidermal growth factor-factor VIII (MFG-E8) in dosage form for treating lung injury. The invention further provides methods of preparing pharmaceutical compositions for treating lung injury, the methods comprising formulating milk fat globule epidermal growth factor-factor VIII (MFG-E8) in a pharmaceutical composition in an amount effective to treat lung injury.

The invention also provides for the use of milk fat globule epidermal growth factor-factor VIII (MFG-E8) for treating lung injury, such as for example, acute lung injury. The invention further provides for the use of milk fat globule epidermal growth factor-factor VIII (MFG-E8) for the preparation of a pharmaceutical composition for treating lung injury.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Materials and Methods

Experimental Model:
Ischemia was induced in C57BL/6J wild-type (WT) mice and MFG-E8 knockout (KO) mice by clamping the superior mesenteric artery (SMA) for 90 minutes under general anesthesia using isofluorane. Mice were resuscitated with 0.5 ml saline and were treated with recombinant murine MFG-E8 (rmMFG-E8) (0.4 mg/kg in 0.5 ml normal saline i.p.) or normal saline (Vehicle). Control animals underwent the same operative procedure with the exception of the SMA clamping (Sham I/R) (n=6). 4 h after reperfusion, animals were anesthetized and EDTA blood (for plasma) and tissue samples were harvested, frozen immediately in liquid nitrogen and stored at −80° C. until measurements. Additional experiments for observation of survival over the course of 24 h were performed (n=15). All experiments were performed in accordance with the guidelines for the use of experimental animals by the National Institutes of Health (Bethesda, Md.) and were previously approved by the Institutional Animal Care and Use Committee of the Feinstein Institute for Medical Research (Manhasset, N.Y.).

MFG-E8 Western Blotting and Gene Expression:

25 μg of protein from spleen and lung samples was fractionated on a Bis-Tris gel and transferred to a 0.22-μm nitrocellulose membrane. Blots were blocked with 5% BSA in Tris-buffered saline containing 0.1% v/v Tween 20 and incubated with hamster anti-mouse MFG-E8 mAb (clone 2422, MBL, Nagoya, Japan). After the incubation with HRP-labeled goat-anti hamster IgG (Santa Cruz, Calif.) in 5% BSA-TBST and washing with TBST, bands were detected using a chemiluminescent peroxidase substrate (ECLplus, Amersham, Little Chalfont, Buckinghamshire, UK) and exposure on a radiograph film. RNA was extracted from spleen and lung tissue samples using TRIzol Reagent (Invitrogen, Carlsbad, Calif.). 5 μg of RNA was reverse transcribed to cDNA using murine leukemia virus reverse transcriptase (Applied Biosystems, Foster City, Calif.) and amplified by qPCR using SYBR green PCR Master Mix (Applied Biosystems). The following primer sets were used: mouse MFG-E8 (forward: 5'-GGG CCT GAA GAA TAA CAC GA-3' (SEQ ID NO:3); reverse: 5'-AGG GCA ACT TGG ACA ACA AC-3' (SEQ ID NO:4)); mouse β-actin (endogenous control; forward: 5'-TGT TAC CAA CTG GGA CGA CA-3' (SEQ ID NO:5); reverse: 5'-GGG GTG TTG AAG GTC TCA AA-3' (SEQ ID NO:6)).

Cytokines and Organ Injury Parameters:

TNF-α, IL-1β, and IL-6, were quantified using specific mouse ELISA kits (BD Pharmingen, Franklin Lakes, N.J.) in EDTA plasma, small intestine and lung tissues. AST, ALT, LDH, lactate, and creatinine blood plasma levels were determined using commercial assay kits (Pointe Scientific, Canton, Mich.).

Histopathology:

Samples of the small intestine (non-necrotic areas) and lungs were fixed in 10% formalin and embedded in paraffin. Tissue blocks were sectioned at a thickness of 5 μm, transferred to glass slides, and stained with hematoxylin/eosin. Morphologic examinations were performed using light microscopy and lung injury analyzed by a blinded, experienced investigator for absent, mild, moderate or severe injury (score 0-3) based on the presence of exudates, hyperemia/congestion, neutrophilic infiltrates, intra-alveolar hemorrhage/debris, and cellular hyperplasia (22). The sum of scores of different animals was averaged. Intestinal injury was scored according to Stallion et al., assessing villus-to-crypt ratio (normal: 5 to 1), lymphocytic infiltrates, epithelial degeneration/necrosis, erosions, glandular dilatation and transmural changes (score 0-4) (23).

Apoptosis Assay:

Tissue samples were de-waxed, incubated with proteinase K, stained using a green fluorescent-tagged TUNEL kit (Roche Diagnostics, Indianapolis, Ind.) counterstained with propidium iodide and examined under a fluorescent microscope. Apoptotic cells appeared green fluorescent on a red background staining.

Tissue Myeloperoxidase (MPO) Assay:

Tissues were homogenized in $KPO_4$ buffer containing 0.5% Hexa-decyl-trimethyl-ammonium bromide (60° C. for 2 h). After centrifuging, supernatant was diluted in reaction solution and ΔOD was measured at 460 nm to calculate MPO activity (24).

Statistics:

Data were expressed as means±SEM and compared by ANOVA using Student-Newman-Keuls' test. Student t test was used if only two groups were present. The survival study was analyzed using the Kaplan-Meier Log-rank test. Differences were considered significant if $P<0.05$.

Results

Figures 1A, 1B:
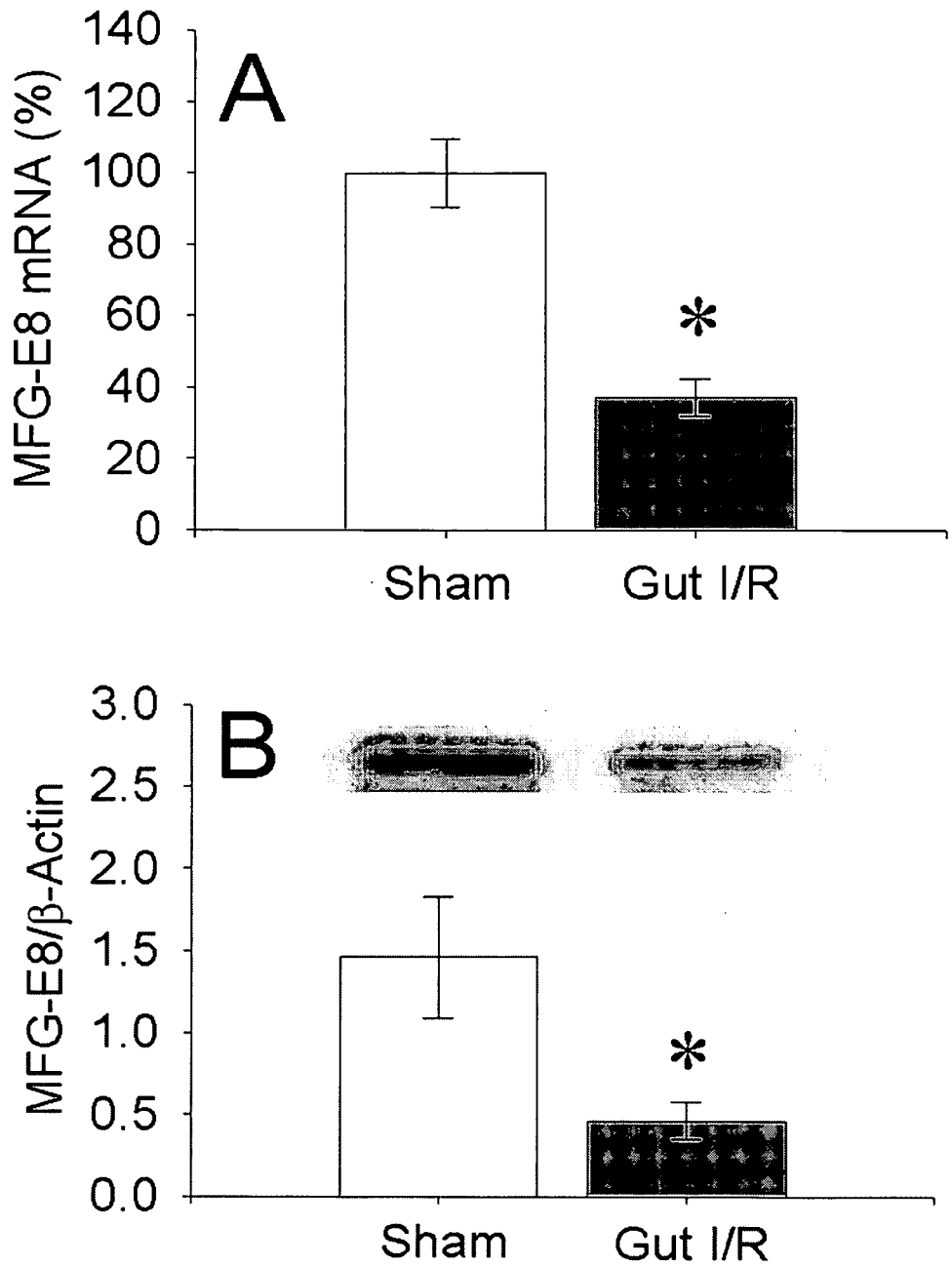
FIG. 1A-1B. Suppression of splenic MFG-E8 after intestinal I/R. The superior mesenteric artery (SMA) was occluded for 90 min followed by 4 h of reperfusion. (A) MFG-E8 mRNA levels in the spleens were measured by qPCR, (B)

Suppression of MFG-E8 in the Spleen after Gut I/R:

To investigate whether MFG-E8 levels are altered after intestinal I/R injury, MFG-E8 mRNA and protein levels were measured in WT mice 4 h post reperfusion after 90-min. ischemia. The results indicate that splenic mRNA levels dropped significantly by on average 63% (FIG. 1A) and protein levels by 68% (FIG. 1B) after gut I/R.

Figures 2A, 2B, 2C, 2D, 2E, 2F:
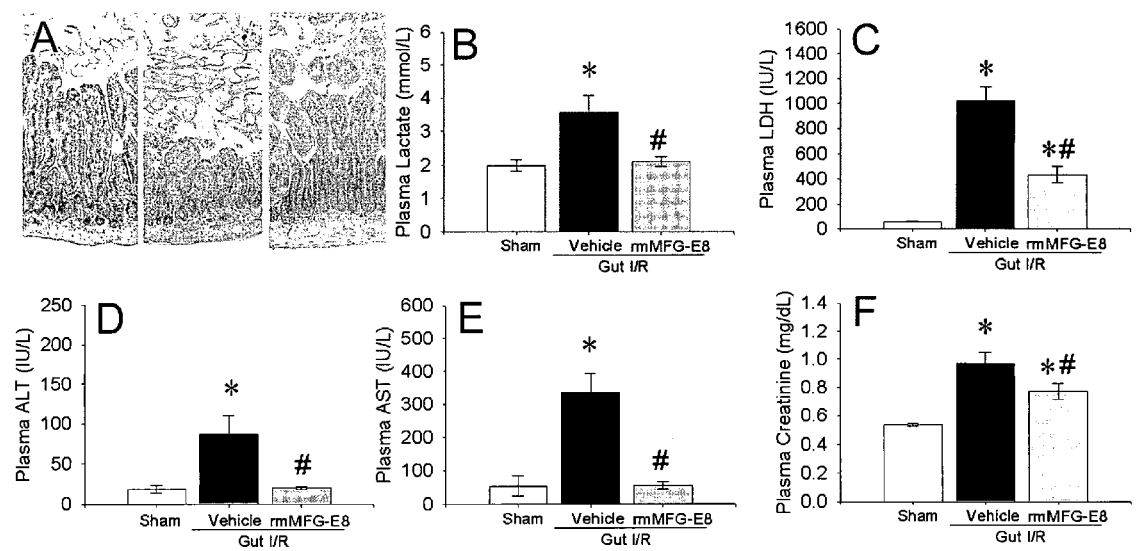

Administration of rmMFG-E8 Attenuates Multiple Organ Injury after Intestinal I/R:

Gut I/R caused widespread macroscopic necrosis with severe enteric mucosal injury (average score 2.25±0.14) in intestinal areas juxtaposed to the macroscopically ischemic bowel (FIG. 2A). Similarly, multiple blood markers of remote organ damage were significantly elevated, including lactate (80% increase), lactate dehydrogenase (LDH) (17.5-fold increase), alanine aminotransferase (ALT) (4.8-fold increase), aspartate aminotransferase (AST) (18.3-fold increase) and creatinine (2-fold increase) compared to sham-operated animals (FIGS. 2B-F), indicating the systemic scale of injury induced in this model. Treatment with one dose of rmMFG-E8 (0.4 μg/20 g BW i.p.) at the beginning of reperfusion largely attenuated I/R-induced multiple organ injury. Histopathologically even large parts of intestine were protected from secondary mucosal damage after treatment (injury score: 1.25±0.14) (FIG. 2A). Treatment with rmMFG-E8 also entirely blocked the elevation of lactate, AST and ALT, while it suppressed LDH and creatinine levels by 58% and 21%, respectively. Hence rmMFG-E8 has a primary protective effect on intestinal mucosa, general perfusion, liver injury, and, to a lesser but still significant extent, on general tissue damage and renal function (FIGS. 2B-F).

Administration of rmMFG-E8 Suppresses the Systemic Inflammatory Response after Intestinal I/R:

Pro-inflammatory cytokines are major contributors in the injury of remote organs after intestinal I/R. Hence it was investigated whether the three cytokines tumor necrosis factor-α (TNF-α), interleukin-6 (IL-6), and interleukin-1β (IL-1β) were affected by the treatment with rmMFG-E8. While blood levels of the cytokines increased significantly after gut I/R (TNF-α by 5.6-fold, IL-1β by 3.9-fold, and IL-6 by 96-fold), rmMFG-E8 dramatically reduced the pro-inflammatory response (by 72%, 42%, and 48%, respectively, FIGS. 3A-C). To investigate whether MFG-E8 influences cytokine production in tissues, cytokine protein levels were analyzed in the small intestine and the lungs using ELISA. Similar suppressive effects of rmMFG-E8 could be found on tissue cytokine levels, suggesting that MFG-E8 confers its anti-inflammatory effect by decreased cytokine production and release from the source of injury as well as from target organs (Table 1).

TABLE 1

Local cytokine suppression by rmMFG-E8 after intestinal I/R

| Organ | Cytokine | Intestinal I/R | | |
|---|---|---|---|---|
| | | Sham | Vehicle | rmMFG-E8 |
| Gut | TNF-α (pg/mg) | 6.5 ± 0.5 | 17.3 ± 3.2* | 6.7 ± 1.4# |
| | IL-6 (pg/mg) | 5.3 ± 0.4 | 14.3 ± 2.1* | 9.6 ± 2.6 |
| | IL-1β (pg/mg) | 24.4 ± 2.6 | 62.5 ± 12.7* | 32.5 ± 8.4# |
| Lung | TNF-α (pg/mg) | 6.2 ± 0.5 | 7.7 ± 1.7 | 5.0 ± 0.2 |
| | IL-6 (pg/mg) | 15.9 ± 3.3 | 33.0 ± 4.5* | 14.7 ± 2.9# |
| | IL-1β (pg/mg) | 33.7 ± 2.3 | 96.1 ± 15.8* | 36.6 ± 2.8# |

C57BL6/J mice underwent SMA I/R for 90 min followed by 4 h reperfusion. 6 mice also received rmMFG-E8 (0.4 μg/20 g BW i.p.) at the beginning of the reperfusion time. Tissue cytokine levels were determined by ELISA and are presented as means ± SEM, *P < 0.05 vs. Sham, #P < 0.05 vs. Vehicle by One-Way ANOVA and Student Newman Keul's test, n = 6.

Administration of rmMFG-E8 Attenuates ALI after Intestinal I/R:

The lungs are one of the organs most severely affected by intestinal I/R injury (25). Histopathological analysis of the lungs showed moderate to severe injury with exudates, congestion, cellular infiltrates and intracellular hemorrhage averaging to a histopathological score of 9.7±0.8 (FIGS. 4A-B). The cell morphology and timing of cellular lung infiltrates were suggestive of a neutrophilic nature. Therefore, myeloperoxidase activity was assessed in the lungs, which was equally elevated by 3.3-fold after gut I/R (FIG. 4C). Treatment with rmMFG-E8 significantly reduced acute lung injury, histopathologically, as well as biochemically (FIGS. 4 A-C). The histopathology score was reduced by 38% and MPO activity was suppressed by 47% (FIGS. 4 B-C).

Pulmonary MFG-E8 Suppression and Apoptosis after Intestinal I/R:

Although Northern blotting revealed the spleen as the major immune competent organ to produce MFG-E8 (20), the lung still expresses significant amounts of MFG-E8 mRNA (about 50% of spleen levels; unpublished observation). Jinushi et al. showed that under normal conditions alveolar macrophages contain most of the MFG-E8 protein in the lungs (26). Quantitative PCR and Western blotting indicated that gut I/R also suppresses MFG-E8 levels by 48% on an mRNA level and by 49% on a protein level (FIGS. 5A-B). At the same time, increased numbers of apoptotic cells were found in the pulmonary tissue by TUNEL staining (FIG. 5C), which was associated with caspase 3 activation (data not shown). Treatment with rmMFG-E8, however, significantly suppressed the number of detectable apoptotic cells in the lungs after gut I/R injury (FIG. 5C).

MFG-E8 Deficiency Increases Pulmonary Inflammation and Deteriorates ALI:

To further elucidate the role of MFG-E8 in gut I/R-mediated ALI, the inflammatory response and lung tissue injury were investigated in MFG-E8-deficient mice. Compared to WT mice, MFG-E8 KO mice produced nearly two-fold increased IL-1β and IL-6 protein levels in the lungs after gut I/R (FIGS. 6A-B). This dramatic increase in pro-inflammatory cytokine production in the lungs was associated with a further deteriorated ALI in MFG-E8 KO mice compared to their WT controls, including increased congestion, exudates, interstitial cellular infiltrates and consolidation (FIGS. 7A-B). Pulmonary neutrophil activity was also significantly increased in MFG-E8 KO mice after gut I/R (FIG. 7C). Overall, this clearly indicates that the absence of MFG-E8 causes more severe inflammation and damage to the lungs in this model.

Treatment with rmMFG-E8 Improves Survival after Intestinal I/R Injury:

The above results suggest that MFG-E8 is beneficial in I/R-mediated injury. Therefore, a survival study was performed in 15 mice receiving rmMFG-E8 at the beginning of reperfusion and compared to control mice treated with normal saline. All of the control mice died within 24 h with a median survival time of 8 h (95% CI: 5.5-10.5 h, FIG. 8). 7 of the 15 animals treated with rmMFG-E8, however, were still alive 24 h after gut I/R (median survival time: 20 h, FIG. 8). This significant improvement in survival time showed that MFG-E8 is protective against multiple organ failure and death caused by bowel I/R injury.

Discussion

The present study demonstrates that intestinal I/R negatively affects lung morphology, increases MPO, and local cytokine production consistent with ALI and that treatment with rmMFG-E8 attenuates organ injury, inflammation, and improves survival. Treated animals also displayed less apoptosis in their lungs, suggesting enhanced MFG-E8-mediated clearance of apoptotic cells. MFG-E8 KO mice showed a dramatically deteriorated ALI and inflammation, providing further evidence for the crucial role of MFG-E8 in I/R-mediated remote organ injury.

Acute lung injury is a syndrome of respiratory failure resulting from acute pulmonary edema and inflammation (2). The incidence of ALI and ARDS combined in the United States was estimated by the National Institutes of Health to be 75 per 100,000 population, and more recent data from Scandinavia showed that ALI alone accounts for roughly 18 per 100,000 population (25, 27). Although mortality rates from ALI and ARDS decreased in the past 20-30 years, they still remain unacceptably high (25). Multiple causes can lead to ALI in patients, including sepsis, severe trauma with shock and multiple transfusions (25). Under these pathological conditions, ALI is driven by an overwhelming systemic inflammatory response and often occurs in conjunction with failure of other organs (3). Intestinal ischemia due to transient obliteration of the SMA, for example, causes vast local tissue injury and the reperfusion of the ischemic bowel leads to a tremendous activation of the inflammatory response, leading to a very severe clinical picture with multiple organ failure including ALI (28). Pathophysiologically, ALI is associated with alveolar exudates and bleeding, influx and activation of immune cells with the release of abundant cytokines and enzymes, which can be further complicated by infection and ventilation-induced injury (3, 25). Impaired barrier function of the lung epithelium and endothelium play a major role in the development of ALI and ARDS and one key aspect of this failure is the loss of cells through apoptosis (2). Particularly type II pneumocytes undergo apoptosis mediated by the activation of the Fas-ligand—Fas pathway and the activation of caspase-3 (12, 13), and it is very likely that the nature of apoptotic cells in the present experiments is epithelial, too. Especially cytokines like IL-1β or TNF-α have been reported to play a major role in apoptosis induction in the lungs (9, 14, 15). Mesenteric I/R injury is predominantly mediated by proinflammatory mediators released from the reperfused intestine, possibly contributing to the induction of apoptosis in remote organs (29). However, the role of reactive oxygen species in the induction of post I/R pulmonary cell death should not be underestimated (30). Apoptosis of type II alveolar pneumocytes directly causes pulmonary edema and reduces the production of surfactant. However, apoptosis plays a role beyond the initial phase of tissue injury, as it is central to the imbalances between inflammatory resolution and the progression of ALI later in the disease (31). Controlled tissue repair through the modulation of apoptosis or apoptotic cell phagocytosis may prevent lung fibrosis, the progression in the disease and its overall severity (2, 12, 25, 31).

MFG-E8 is a secretory molecule and mainly produced in the spleen. It can, however, also be found in significant amounts in lymph nodes and in the lungs (20, 26). It is mainly produced by macrophages and dendritic cells and has so far been mainly linked to the opsonization of apoptotic cells. Hanayama et al. discovered that MFG-E8 plays a major role in the clearance of apoptotic B cells in the spleen, which prevents the development of autoimmune diseases (16, 19, 20). In mice, MFG-E8 is a 64 kDa glycoprotein with two EGF-like domains (E1 and E2) containing an RGD-motif that can bind certain integrins (vitronectin receptor, $\alpha v \beta 3$ or $\alpha v \beta 5$) that are highly expressed on macrophages and other phagocytic cells. This domain is separated by a P/T-rich region from two coagulation factor V/VIII-like domains (C1 and C2) that have a strong affinity to phosphatidylserine (PS). These properties make it an important factor in binding apoptotic cells that express high amounts of PS on their surface to phagocytes (19). While PS-expressing apoptotic cells can also bind to other receptors on macrophages, including the putative PS receptor and CD36, the binding to $\alpha v \beta 3$ or $\alpha v \beta 5$-integrins via MFG-E8 is required to induce their engulfment (19). At very high concentrations, MFG-E8 has also been shown to modulate the intrinsic coagulation cascade due to its competition for PS binding sites and to increase the prothrombin time by 50% (32). It is also involved in the VEGF-dependent neovascularization (33) and in the migration of enterocytes and intestinal repair (34). It has been proposed to be beneficial in atherosclerosis (35) and Alzheimer's disease (36), although the mechanism is still unclear. MFG-E8 clearly plays an important role at the interface between phagocytosis of apoptotic cells and inflammation in chronic and acute inflammatory diseases. MFG-E8-dependent increase in apoptotic cell clearance can prevent deaths from sepsis (21).

Sepsis and mesenteric I/R injury share the fact that both lead to a systemic inflammatory response (23). Gut I/R has also been shown to lead to increased microbial translocation and the release of bacterial toxins into the blood stream (4, 5). Activation of toll-like receptors has indeed been shown to suppress MFG-E8 levels in vitro and in vivo ((26) and unpublished data). So far, only granulocyte/monocyte colony stimulating factor is known to modulate MFG-E8 expression (26). Whether other cytokines have the potential to change MFG-E8 expression and at what kinetics is currently unknown. The present studies have shown a clear suppression of MFG-E8 in the spleen and in lungs 4 h after reperfusion of the 90-min-ischemic gut. The suppression of MFG-E8 by 50%, as found in the lungs of gut I/R mice, appears to be sufficient to impair phagocytosis of apoptotic cells as previously reported in a sepsis model (21). Although the number of apoptotic cells in the lung was not very high, the cells affected are most likely type II pneumocytes, which would contribute to the progression of ALI (9). Treatment with rmMFG-E8 reduced the number of apoptotic cells and suppressed local inflammation. Decreased apoptosis is not mediated by a direct antiapoptotic effect but through the stimulation of apoptotic cell clearance (21). The present studies also found that the pulmonary injury after gut I/R was attenuated after treatment with rmMFG-E8 as evidenced by improved tissue injury and decreased neutrophil activity. While the proinflammatory cytokines were generally suppressed in the small intestine, lungs, and blood after treatment with rmMFG-E8, there was no difference in the cytokine levels of the intestine and the blood between MFG-E8 KO mice and their WT controls 4 h after reperfusion of the ischemic bowel. The lungs, however, demonstrated a 2-fold increase of IL-6 and IL-1β in the MFG-E8 KO mice indicating that in this model deficiency of MFG-E8 mostly affects the lungs. This is quite interesting as this implies that the lungs are not only a victim of the systemic inflammatory response but greatly contribute to the inflammation.

How this anti-inflammatory effect of MFG-E8 works in this ALI model still remains unknown. The clearance of apoptotic cells clearly suppresses the inflammatory responsiveness of macrophages (17, 31). As alveolar macrophages are potentially the cells that lose MFG-E8 after I/R, these may be primed by the deficit of the suppressive effect of apoptotic cell phagocytosis to produce and release more inflammatory cytokines (17). This could explain the increased inflammation and injury in the lungs and the release of inflammatory mediators into the circulation. The mechanism could involve intracellular anti-inflammatory pathways in the alveolar macrophages, the release of anti-inflammatory cytokines (such as IL-10 and TGF-β) (31, 37) and the generation of immunosuppressive cells, such as regulatory T cells (26, 35). The mere removal of dying cells that have the potential to release toxic and proinflammatory contents may be another potential mechanism by which MFG-E8 confers its beneficial effect (38).

The present studies have clearly shown that MFG-E8 is anti-inflammatory in vivo and protects from multiple organ dysfunctions including lung injury after gut I/R. This is associated with a significantly improved chance of survival. Thus, MFG-E8 may serve as a novel treatment option for ALI after I/R, or of other etiology, by promoting tissue repair and positively affecting morbidity and mortality in affected patients.

REFERENCES

1. Tendler D A. Acute intestinal ischemia and infarction. *Semin Gastrointest Dis* 2003; 14:66-76.
2. Matthay M A, Zimmerman G A, Esmon C, Bhattacharya J, Coller B, Doerschuk C M, Floros J, Gimbrone M A, Jr., Hoffman E, Hubmayr R D, et al. Future research directions in acute lung injury: Summary of a national heart, lung, and blood institute working group. *Am J Respir Crit Care Med* 2003; 167:1027-1035.
3. Bellingan G J. The pulmonary physician in critical care * 6: The pathogenesis of ali/ards. *Thorax* 2002; 57:540-546.
4. Gathiram P, Gaffin S L, Wells M T, Brock-Utne J G. Superior mesenteric artery occlusion shock in cats: Modification of the endotoxemia by antilipopolysaccharide antibodies (anti-lps). *Circ Shock* 1986; 19:231-237.
5. Souza D G, Vieira A T, Soares A C, Pinho V, Nicoli J R, Vieira L Q, Teixeira M M. The essential role of the intestinal microbiota in facilitating acute inflammatory responses. *J Immunol* 2004; 173:4137-4146.
6. Tamion F, Richard V, Lyoumi S, Daveau M, Bonmarchand G, Leroy J, Thuillez C, Lebreton J P. Gut ischemia and mesenteric synthesis of inflammatory cytokines after hemorrhagic or endotoxic shock. *Am J Physiol* 1997; 273: G314-321.
7. Artigas A, Bernard G R, Carlet J, Dreyfuss D, Gattinoni L, Hudson L, Lamy M, Marini J J, Matthay M A, Pinsky M R, et al. The american-european consensus conference on ards, part 2: Ventilatory, pharmacologic, supportive therapy, study design strategies, and issues related to recovery and remodeling. Acute respiratory distress syndrome. *Am J Respir Crit Care Med* 1998; 157:1332-1347.

8. Shah K A, Shurey S, Green C J. Apoptosis after intestinal ischemia-reperfusion injury: A morphological study. *Transplantation* 1997; 64:1393-1397.
9. An S, Hishikawa Y, Liu J, Koji T. Lung injury after ischemia-reperfusion of small intestine in rats involves apoptosis of type ii alveolar epithelial cells mediated by tnf-alpha and activation of bid pathway. *Apoptosis* 2007; 12:1989-2001.
10. Collange O, Fabienne T, Nathalie R, Christian T, Vincent R, Bertrand D, Didier P. Pulmonary apoptosis after supraceliac aorta clamping in a rat model. *J Surg Res* 2005; 129:190-195.
11. Mura M, Andrade C F, Han B, Seth R, Zhang Y, Bai X H, Waddell T K, Hwang D, Keshavjee S, Liu M. Intestinal ischemia-reperfusion-induced acute lung injury and oncotic cell death in multiple organs. *Shock* 2007; 28:227-238.
12. Perl M, Chung C S, Perl U, Lomas-Neira J, de Paepe M, Cioffi W G, Ayala A. Fas-induced pulmonary apoptosis and inflammation during indirect acute lung injury. *Am J Respir Crit Care Med* 2007; 176:591-601.
13. Perl M, Lomas-Neira J, Chung C S, Ayala A. Acute lung injury: Neutrophils, epithelial cell death & inflammation: A unifying hypothesis. *Mol Med* 2008.
14. Seitz D H, Peri M, Mangold S, Neddermann A, Braumuller S T, Zhou S, Bachem M G, Huber-Lang M S, Knoferl M W. Pulmonary contusion induces alveolar type 2 epithelial cell apoptosis: Role of alveolar macrophages and neutrophils. *Shock* 2008; [Epub ahead of print].
15. Flierl M A, Perl M, Rittirsch D, Bartl C, Schreiber H, Fleig V, Schlaf G, Liener U, Brueckner U B, Gebhard F, et al. The role of c5a in the innate immune response after experimental blunt chest trauma. *Shock* 2008; 29:25-31.
16. Hanayama R, Miyasaka K, Nakaya M, Nagata S. Mfg-e8-dependent clearance of apoptotic cells, and autoimmunity caused by its failure. *Curr Dir Autoimmun* 2006; 9:162-172.
17. Hart S P, Dransfield I, Rossi A G. Phagocytosis of apoptotic cells. *Methods* 2008; 44:280-285.
18. Wu Y, Tibrewal N, Birge R B. Phosphatidylserine recognition by phagocytes: A view to a kill. *Trends Cell Biol* 2006; 16:189-197.
19. Hanayama R, Tanaka M, Miwa K, Shinohara A, Iwamatsu A, Nagata S. Identification of a factor that links apoptotic cells to phagocytes. *Nature* 2002; 417:182-187.
20. Hanayama R, Tanaka M, Miyasaka K, Aozasa K, Koike M, Uchiyama Y, Nagata S. Autoimmune disease and impaired uptake of apoptotic cells in mfg-e8-deficient mice. *Science* 2004; 304:1147-1150.
21. Miksa M, Wu R, Dong W, Das P, Yang D, Wang P. Dendritic cell-derived exosomes containing milk fat globule epidermal growth factor-factor viii attenuate proinflammatory responses in sepsis. *Shock* 2006; 25:586-593.
22. Bachofen M, Weibel E R. Structural alterations of lung parenchyma in the adult respiratory distress syndrome. *Clin Chest Med* 1982; 3:35-56.
23. Stallion A, Kou T D, Latin S Q, Miller K A, Dahms B B, Dudgeon D L, Levine A D. Ischemia/reperfusion: A clinically relevant model of intestinal injury yielding systemic inflammation. *J Pediatr Surg* 2005; 40:470-477.
24. Day Y J, Marshall M A, Huang L, McDuffie M J, Okusa M D, Linden J. Protection from ischemic liver injury by activation of a2a adenosine receptors during reperfusion: Inhibition of chemokine induction. *Am J Physiol Gastrointest Liver Physiol* 2004; 286:G285-293.
25. Ware L B, Matthay M A. The acute respiratory distress syndrome. *N Engl J Med* 2000; 342:1334-1349.
26. Jinushi M, Nakazaki Y, Dougan M, Carrasco D R, Mihm M, Dranoff G. Mfg-e8-mediated uptake of apoptotic cells by apcs links the pro- and antiinflammatory activities of gm-csf. *J Clin Invest* 2007; 117:1902-1913.
27. Luhr O R, Antonsen K, Karlsson M, Aardal S, Thorsteinsson A, Frostell C G, Bonde J. Incidence and mortality after acute respiratory failure and acute respiratory distress syndrome in sweden, denmark, and iceland. The arf study group. *Am J Respir Crit Care Med* 1999; 159:1849-1861.
28. Hart M L, Ceonzo K A, Shaffer L A, Takahashi K, Rother R P, Reenstra W R, Buras J A, Stahl G L. Gastrointestinal ischemia-reperfusion injury is lectin complement pathway dependent without involving clq. *J Immunol* 2005; 174:6373-6380.
29. Tang P S, Mura M, Seth R, Liu M. Acute lung injury and cell death: How many ways can cells die? *Am J Physiol Lung Cell Mol Physiol* 2008; 294:L632-641.
30. Nanavaty U B, Pawliczak R, Doniger J, Gladwin M T, Cowan M J, Logun C, Shelhamer J H. Oxidant-induced cell death in respiratory epithelial cells is due to DNA damage and loss of atp. *Exp Lung Res* 2002; 28:591-607.
31. Huynh M L, Fadok V A, Henson P M. Phosphatidylserine-dependent ingestion of apoptotic cells promotes tgf-beta1 secretion and the resolution of inflammation. *J Clin Invest* 2002; 109:41-50.
32. Shi J, Gilbert G E. Lactadherin inhibits enzyme complexes of blood coagulation by competing for phospholipid-binding sites. *Blood* 2003; 101:2628-2636.
33. Silvestre J S, Thery C, Levy B, Tedgui A, Amigorena S, Mallat Z. [lactadherin promotes vegf-dependent neovascularization]. *Med Sci (Paris)* 2005; 21:683-685.
34. Bu H F, Zuo X L, Wang X, Ensslin M A, Koti V, Hsuch W, Raymond A S, Shur B D, Tan X D. Milk fat globule-egf factor 8/lactadherin plays a crucial role in maintenance and repair of murine intestinal epithelium. *J Clin Invest* 2007; 117:3673-3683.
35. Ait-Oufella H, Kinugawa K, Zoll J, Simon T, Boddaert J, Heeneman S, Blanc-Brude O, Barateau V, Potteaux S, Merval R, et al. Lactadherin deficiency leads to apoptotic cell accumulation and accelerated atherosclerosis in mice. *Circulation* 2007; 115:2168-2177.
36. Boddaert J, Kinugawa K, Lambert J C, Boukhtouche F, Zoll J, Merval R, Blanc-Brude O, Mann D, Ben C, Vilar J, et al. Evidence of a role for lactadherin in alzheimer's disease. *Am J Pathol* 2007; 170:921-929.
37. Asano K, Miwa M, Miwa K, Hanayama R, Nagase H, Nagata S, Tanaka M. Masking of phosphatidylserine inhibits apoptotic cell engulfment and induces autoantibody production in mice. *J Exp Med* 2004; 200:459-467.
38. Krysko D V, Vanden Berghe T, D'Herde K, Vandenabeele P. Apoptosis and necrosis: Detection, discrimination and phagocytosis. *Methods* 2008; 44:205-221.
39. Kieber-Emmons T, Murali R, Greene M I. Therapeutic peptides and peptidomimetics. Curr Opin Biotechnol. 1997 August; 8(4):435-41.
40. Ripka A S, Rich D H. Peptidomimetic design. Curr Opin Chem Biol. 1998 August; 2(4):441-452.
41. Sanderson P E. Small, noncovalent serine protease inhibitors. Med Res Rev. 1999 March; 19(2):179-97.

APPENDIX

SEQ ID Nos

SEQ ID NO:1—human MFG-E8—from GenBank NP005919
1 mprprllaal cgallcapsl lvaldicskn pchngglcee isqevrgdvf psytctclkg
61 yagnhcetkc veplgmengn iansqiaass vrvtflglqh wvpelarinr agmvnawtps
121 snddnpwiqv nllrrmwvtg vvtqgasrla sheylkafkv ayslnghefd fihdvnkkhk
181 efvgnwnkna vhvnlfetpv eaqyvrlypt schtactlrf ellgcelngc anplglknns
241 ipdkqitass syktwglhlf swnpsyarld kqgnfnawva gsygndqwlq vdlgsskevt
301 giitqgarnf gsvqfvasyk vaysndsanw teyqdprtgs skifpgnwdn hshkknlfet
361 pilaryvril pvawhnrial rlellgc SEQ ID NO:2—mouse MFG-E8—from GenBank NP032620
1 mqvsrvlaal cgmllcasgl faasgdfcds slclnggtcl tgqdndiycl cpegftglvc
61 netergpcsp npcyndakcl vtldtqrgdi fteyicqcpv gysgihcete tnyynldgey
121 mfttavpnta vptpaptpdl snnlasrcst qlgmeggaia dsqisasyvy mgfmglqrwg
181 pelarlyrtg ivnawhasny dskpwiqvnl lrkmrvsgvm tqgasragra eylktfkvay
241 sldgrkfefi qdesggdkef lgnldnnslk vnmfnptlea qyirlypvsc hrgctlrfel
301 lgcelhgcle plglknntip dsqmsasssy ktwnlrafgw yphlgrldnq gkinawtaqs
361 nsakewlqvd lgtqrqvtgi itqgardfgh iqyvesykva hsddgvqwtv yeeqgsskvf
421 qgnldnnshk knifekpfma ryvrvlpvsw hnritlrlel lgc

---

What is claimed is:

1. A method of attenuating organ injury after ischemia/reperfusion in a subject comprising administering to the subject a milk fat globule epidermal growth factor-factor VIII (MFG-E8) having a sequence at least 99% identical to SEQ ID NO:1 or SEQ ID NO:2 in an amount effective to attenuate organ injury after ischemia/reperfusion.

2. The method of claim 1, wherein the MFG-E8 has an amino acid sequence at least 99% identical to SEQ ID NO:1.

3. The method of claim 1, wherein the MFG-E8 has an amino acid sequence identical to SEQ ID NO:1.

4. The method of claim 1, wherein the MFG-E8 has an amino acid sequence at least 99% identical to SEQ ID NO:2.

5. The method of claim 1, wherein the MFG-E8 has an amino acid sequence identical to SEQ ID NO:2.

6. The method of claim 1, wherein the MFG-E8 is recombinant MFG-E8.

7. The method of claim 1, wherein the organ is one or more of gastrointestinal tract, liver, lung, kidney, heart, brain, spinal cord or crushed limb.

8. The method of claim 1, where the organ injury is acute lung injury.

9. The method of claim 1, wherein the ischemia/reperfusion is one or more of gastrointestinal tract, liver, lung, kidney, heart, brain, spinal cord or crushed limb ischemia/reperfusion.

10. The method of claim 1, wherein the ischemia/reperfusion is intestinal ischemia/reperfusion.

11. A method of treating lung injury after ischemia/reperfusion in a subject comprising administering to the subject a milk fat globule epidermal growth factor-factor VIII (MFG-E8) having a sequence at least 99% identical to SEQ ID NO:1 or SEQ ID NO:2 in an amount effective to treat lung injury after ischemia/reperfusion.

12. The method of claim 11, wherein the MFG-E8 has an amino acid sequence at least 99% identical to SEQ ID NO:1.

13. The method of claim 11, wherein the MFG-E8 has an amino acid sequence identical to SEQ ID NO:1.

14. The method of claim 11, wherein the MFG-E8 has an amino acid sequence at least 99% identical to SEQ ID NO:2.

15. The method of claim 11, wherein the MFG-E8 has an amino acid sequence identical to SEQ ID NO:2.

16. The method of claim 11, wherein the MFG-E8 is recombinant MFG-E8.

* * * * *

```
                           SEQUENCE LISTING

<160> NUMBER OF SEQ ID NOS: 6

<210> SEQ ID NO 1
<211> LENGTH: 387
<212> TYPE: PRT
<213> ORGANISM: Homo Sapiens

<400> SEQUENCE: 1

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
```

```
                    245                 250                 255
Leu His Leu Phe Ser Trp Asn Pro Ser Tyr Ala Arg Leu Asp Lys Gln
                260                 265                 270

Gly Asn Phe Asn Ala Trp Val Ala Gly Ser Tyr Gly Asn Asp Gln Trp
            275                 280                 285

Leu Gln Val Asp Leu Gly Ser Ser Lys Glu Val Thr Gly Ile Ile Thr
    290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
    370                 375                 380

Leu Gly Cys
385

<210> SEQ ID NO 2
<211> LENGTH: 463
<212> TYPE: PRT
<213> ORGANISM: Mouse Sp.

<400> SEQUENCE: 2

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Thr Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
    130                 135                 140

Ala Ser Arg Cys Ser Thr Gln Leu Gly Met Glu Gly Gly Ala Ile Ala
145                 150                 155                 160

Asp Ser Gln Ile Ser Ala Ser Tyr Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp His Ala Ser Asn Tyr Asp Ser Lys Pro Trp Ile Gln Val
        195                 200                 205

Asn Leu Leu Arg Lys Met Arg Val Ser Gly Val Met Thr Gln Gly Ala
    210                 215                 220
```

-continued

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
            245                 250                 255

Asp Lys Glu Phe Leu Gly Asn Leu Asp Asn Asn Ser Leu Lys Val Asn
        260                 265                 270

Met Phe Asn Pro Thr Leu Glu Ala Gln Tyr Ile Arg Leu Tyr Pro Val
    275                 280                 285

Ser Cys His Arg Gly Cys Thr Leu Arg Phe Glu Leu Leu Gly Cys Glu
290                 295                 300

Leu His Gly Cys Leu Glu Pro Leu Gly Leu Lys Asn Asn Thr Ile Pro
305                 310                 315                 320

Asp Ser Gln Met Ser Ala Ser Ser Tyr Lys Thr Trp Asn Leu Arg
            325                 330                 335

Ala Phe Gly Trp Tyr Pro His Leu Gly Arg Leu Asp Asn Gln Gly Lys
            340                 345                 350

Ile Asn Ala Trp Thr Ala Gln Ser Asn Ser Ala Lys Glu Trp Leu Gln
        355                 360                 365

Val Asp Leu Gly Thr Gln Arg Gln Val Thr Gly Ile Ile Thr Gln Gly
370                 375                 380

Ala Arg Asp Phe Gly His Ile Gln Tyr Val Glu Ser Tyr Lys Val Ala
385                 390                 395                 400

His Ser Asp Asp Gly Val Gln Trp Thr Val Tyr Glu Glu Gln Gly Ser
            405                 410                 415

Ser Lys Val Phe Gln Gly Asn Leu Asp Asn Asn Ser His Lys Lys Asn
        420                 425                 430

Ile Phe Glu Lys Pro Phe Met Ala Arg Tyr Val Arg Val Leu Pro Val
        435                 440                 445

Ser Trp His Asn Arg Ile Thr Leu Arg Leu Glu Leu Leu Gly Cys
450                 455                 460

<210> SEQ ID NO 3
<211> LENGTH: 20
<212> TYPE: DNA
<213> ORGANISM: Artificial Sequence
<220> FEATURE:
<223> OTHER INFORMATION: Primer directed to mouse MFG-E8

<400> SEQUENCE: 3
gggcctgaag aataacacga                                               20

<210> SEQ ID NO 4
<211> LENGTH: 20
<212> TYPE: DNA
<213> ORGANISM: Artificial Sequence
<220> FEATURE:
<223> OTHER INFORMATION: Primer directed to mouse MFG-E8

<400> SEQUENCE: 4
agggcaactt ggacaacaac                                               20

<210> SEQ ID NO 5
<211> LENGTH: 20
<212> TYPE: DNA
<213> ORGANISM: Artificial Sequence
<220> FEATURE:
<223> OTHER INFORMATION: Primer directed to mouse beta-actin

<400> SEQUENCE: 5

```
tgttaccaac tgggacgaca                                               20

<210> SEQ ID NO 6
<211> LENGTH: 20
<212> TYPE: DNA
<213> ORGANISM: Artificial Sequence
<220> FEATURE:
<223> OTHER INFORMATION: Primer directed to mouse beta actin

<400> SEQUENCE: 6
ggggtgttga aggtctcaaa                                               20
```